United States Patent [19]

Jansen

[11] 4,174,632
[45] Nov. 20, 1979

[54] LIQUID SAMPLER

[75] Inventor: Adolf E. Jansen, Rotterdam, Netherlands

[73] Assignee: Douwes International B.V., Pijnacker, Netherlands

[21] Appl. No.: 920,521

[22] Filed: Jun. 29, 1978

[30] Foreign Application Priority Data

Jul. 6, 1977 [NL] Netherlands .................. 7707477

[51] Int. Cl.² ........................................... G01N 1/10
[52] U.S. Cl. ........................................... 73/422 R
[58] Field of Search ............ 73/422 R, 421 R, 421 B

[56] References Cited

U.S. PATENT DOCUMENTS

| 3,383,923 | 5/1968 | Conche et al. ............. 73/421 B |
| 4,118,987 | 10/1978 | Zeh ............................. 73/422 R |

FOREIGN PATENT DOCUMENTS 549706 10/1975 U.S.S.R. .................. 73/422 R

*Primary Examiner*—S. Clement Swisher
*Attorney, Agent, or Firm*—Ladas, Parry, Von Gehr, Goldsmith & Deschamps

[57] ABSTRACT

The problem encountered with filling sample bottles with the aid of a known device, that dangerous liquids can only be manipulated by using a branch line to a closed casing, has according to the invention be solved by placing an injection needle within a cap which is fixedly connected to the process portion and has an internal surface which corresponds with the external surface of the sample bottle, which cap preferably also has a slot so that a worker can see to which extent the bottle is filled.

5 Claims, 1 Drawing Figure

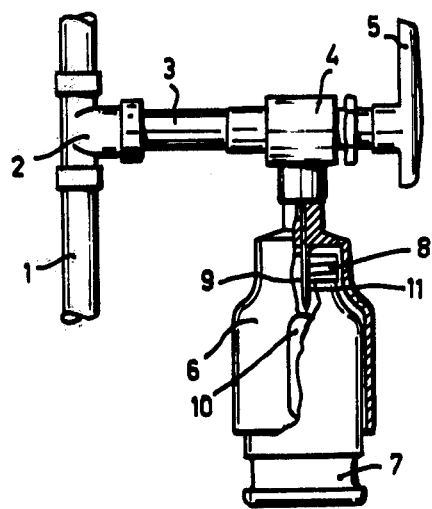

LIQUID SAMPLER

The present invention relates to a sampler which can be connected to a manufacturing process portion, like a process line or a barrel, to take samples safely, the connection between the process portion and the interior of the collection container being effected by sticking an injection needle through a septum in the opening of the collection container.

Such a sampler is known from Dutch Pat. No. 94,040. Said sampler comprises a cap which has to be removed if a sampler has to be brought into an evacuated bottle or flask. This does not provide the possibility to take liquid samples safely if most dangerous liquids are concerned, for instance in phosgene works, and for that reason when taking samples in such works one still has to resort to leading the branch line to a closed casing, having a connection for the discharge of escaped vapours to a closed container. But also at other points, especially in process industries, the installations need quality control for the products and semi-finnished products at various places.

It is the object of the present invention to give a solution for the above-indicated problems, dangers and disadvantages of the known state of the art.

According to the present invention this is achieved in that the injection needle is located within a cap which is fixedly connected to the process portion and has an internal surface which corresponds with the external surface of the collection container.

The length of the cap is preferably somewhat shorter than the length of the collection container, so that the collection container, for instance a flask, can be manually pressed into the cap from below, so that the needle, present there, pierces the septum in the neck of the flask.

For strength's sake the cap has to be made of solid material, like teflon. In practice an efficient embodiment appeared to be a cap of stainless steel or the like material, in which especially the strength of the connection to the branch line seems to turn the scale. In order to enable a worker to control well whether the flask is filled, it is suggested according to the present invention, that in said cap at least a slot is provided.

The invention will be further elucidated on the basis of the drawing, in which by way of example a side view, partially in cross-section, is given of an embodiment of a sampler according to the present patent application.

The process line 1 comprises a T-shaped portion 2 which is connected to a branch line 3 which leads to a valve 4 which can be opened and closed by a tap 5.

The valve 4 comprises a cap 6 having its inner surface corresponding to the exterior surface of the sample flask 7, which has a septum 8 in its opening which can be pierced by an injection needle 9 placed within the cap 6. In order to be able to control the filling course of the flask the wall of the cap is provided at least with a slot 10. Desaeration of the flask takes place via a desaeration needle 11 placed against the injection needle 9, said first-mentioned needle debouching into the cap 6 above the septum 8. It is also possible, however, that the air, possibly polluted by gas, vapour or liquid coming from or belonging to the medium to be sampled, is exhaused or discharged. The desaeration needle 11 can be located separately and communicate with a hole in the cap of the sampler which has to be connected either or not via a return valve, with a return line. Said line generally returns the above-mentioned polluted air and/or the medium back in process or to a special store.

The sampler according to the present invention can be operated as follows:

a sample flask, provided with a special cover, is inserted into the cap. The cover is being pierced by the injection needle. The flask can be filled or not, which may be important when industrially filling the flasks completely hygienically in the pharmaceutical industry. If the tap 5 is opened, the medium runs into the flask. Through the slots 10, made in the cap the worker can see whether the required quantity is present and after the tap has been closed again the flask 7 is taken out of the cap. The septum 8 in the special cover automatically closes the flasks well then.

The cap can be made of various materials, but the following materials are preferably used: stainless stell, teflon monel, hasteloy or the like materials. The injection needles are preferably made of stainless steel.

It is remarked that within the scope of the following claims also countless other embodiments are possible than are shown in the drawing. Especially, it is also possible not to combine the cap with the tap, whereas the flask need not necessarily be provided with a neck.

What is claimed is:

1. A sampler which can be connected to a manufacturing process portion for taking samples therefrom, comprising a tap in a branch line of the process portion, and a cap which is integrally formed with the tap and is adapted to receive a collection container which is inserted into the cap, the configuration of the internal surface of the cap corresponding to the configuration of the external surface of the collection container, and the sampler further comprising an injection needle disposed within the cap for penetrating a septum in the opening of the collection container when the container is inserted into the cap, the needle being in communication with the tap for introducing a sample of fluid from said branch line into the container.

2. A sampler as claimed in claim 1, wherein the cap is made of opaque material but is formed with a slot to permit viewing of the filling of the collection container.

3. A sampler as claimed in claim 1 or 2, further comprising a desaeration needle which debouches into the interior of the cap to enable desaeration of the container.

4. A sampler as claimed in claim 3, wherein the desaeration needle is connected through the wall of the cap to a desaeration line.

5. In combination, a sampler as claimed in claim 1 and a collection container, wherein the length of the cap is shorter than that of the collection container, so as to ensure that the container protrudes from the cap even when fully inserted into the cap.

* * * * *